United States Patent [19]

Peroutka et al.

[11] Patent Number: 5,229,412

[45] Date of Patent: Jul. 20, 1993

[54] METHOD FOR RELIEVING ANXIETY USING 5-HYDROXYTRYPTAMINE-1A-RECEPTOR-BINDING COMPOUNDS

[75] Inventors: Stephen J. Peroutka, Stanford, Calif.; Josef Pitha, Baltimore, Md.

[73] Assignee: The Board of Trustees of the Leland Stanford Junior University, Stanford, Calif.

[21] Appl. No.: 173,442

[22] Filed: Mar. 25, 1988

[51] Int. Cl.$^5$ ................ A61K 31/135; A61K 31/405
[52] U.S. Cl. .................................... 514/415; 514/659
[58] Field of Search ......................... 548/503; 514/415

[56] References Cited

U.S. PATENT DOCUMENTS

| | | | |
|---|---|---|---|
| 4,235,919 | 11/1980 | Berthold, I | 548/503 |
| 4,304,915 | 12/1981 | Berthold, III | 548/503 |
| 4,361,562 | 11/1982 | Berthold, II | 548/505 |
| 4,704,394 | 11/1987 | Geho | 514/415 |

FOREIGN PATENT DOCUMENTS

| | | |
|---|---|---|
| 0025111 | 7/1980 | European Pat. Off. . |
| 0200915 | 4/1986 | European Pat. Off. . |
| 83/01772 | 5/1983 | World Int. Prop. O. . |

OTHER PUBLICATIONS

Gozlan, et al., "Identification of Presynaptic Serotonin Autoreceptors Using a New Ligand: 3H-PAT" *Nature* 305: 140-143 (1983).

Peroutka, et al., "Selective Interation of Novel Anxiolytics with 5-Hydroxytryptamine$_{1A}$ Receptors" *Biol. Psychiatry* 20: 971-979 (1985).

Hiner, et al., "Antimigraine Drug Interactions with 5-Hydroxytryptamine$_{1A}$ Receptors" *Annals of Neurology* 19: 511-513 (1986).

Peroutka, et al., "Multiple Serotonin Receptors: Differential Binding of $^3$H-Serotonin, $^3$H-Lysergic acid diethylamide, and $^3$H-Spiroperidol" *Molecular Pharmacology* 16: 687-699 (1979).

Pitha, et al., "Affinity labels for β-Adrenoreceptors: Preparation and Properties of Alkylating β-Blockers Derived from Indole" *J. Medicinal Chem.* 30(4): 612-615 (1987).

Kwong, et al., "Differential Interactions of 'Prosexual' Drugs With 5-Hydroxytryptamine$_{1A}$ in β$_2$-adrenergic Receptors," *Behaviorial Neuroscience* 100(5): 664-668 (1986).

Chorev et al., "N-Bromoacetylaminocyanopindolol: A Highly Potent β-Adrenergic Affinity Label Blocks Irreversibly A Nonprotein Component33 TM Tightly Associated with the Receptor" *Chemical Abstracts*, 102(13): 54 (1985).

Amlaiky et al., "Synthesis and Irreversible β-Adrenergic Blockade with a Bromoacetamido Derivative of Betaxolol" *Chemical Abstracts* 104(19): 632 (1986).

Liptak, et al., "Alkylating β-Blockers: Activity of Isomeric Bromoacetyl Alprenolol Methanes", *Chemical Abstracts* 103(25): 921 (1985).

Burgermeister, et al., "A Carbene-Generating Photaffinity Probe for β-Adrenergic Receptors", *Chemical Abstracts* 98(23): 85 (1983).

*Primary Examiner*—Robert A. Wax
*Assistant Examiner*—Eric Grimes
*Attorney, Agent, or Firm*—Richard L. Neeley

[57] ABSTRACT

Compounds that selectively bind 5-HT$_{1A}$ receptors in preference to other 5-HT receptors are provided along with methods for their use. Such compounds have the formula

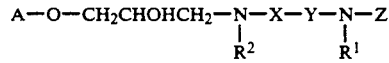

wherein A is an aromatic group selected to provide, with the glycidyl residue that forms the next portion of the molecule, a 5-HT-like portion of the molecule that represents the primary binding site of the molecule with a 5-HT receptor: X represents a quarternary carbon and its attached alkyl groups: Y represents a hydrocarbon linking group: Z represents hydrogen or an organic group containing up to 12 carbon and/or heteroatoms in its skeletal structure: and R$^1$ and R$^2$ independently represent hydrogen or an alkyl group. The aromatic group is most preferably indole or an indole derivative.

17 Claims, No Drawings

METHOD FOR RELIEVING ANXIETY USING 5-HYDROXYTRYPTAMINE-1A-RECEPTOR-BINDING COMPOUNDS

BACKGROUND OF THE INVENTION

1. Field of the Invention

This invention relates to compounds that exhibit binding affinity for 5-hydroxytryptamine-1A receptors and is particularly directed to compounds that interact specifically with such receptors in preference to other 5-hydroxytryptamine receptors and in some cases to β-adrenergic receptors.

2. Description of the Background

5-Hydroxytryptamine (serotonin) is a widely distributed neurotransmitter that stimulates or inhibits a variety of smooth muscles and nerves. The endogenous compound is involved in a wide spectrum of responses including the cardiovascular, respiratory, and gastrointestinal systems.

5-Hydroxytryptamine, often abbreviated 5-HT, operates by interaction with receptors on cell surfaces. There are a number of distinct types of receptors for 5-HT, as evidenced by their wide range of susceptibilities to different blocking drugs. Radioligand-binding studies, principally in brain tissue, have identified two broad 5-HT receptor types. The first is preferentially labeled with [$^3$H]-5-HT and is referred to as 5-HT$_1$ receptors. A second broad class, termed 5-HT$_2$, is preferentially labeled with [$^3$H]-spiperone. However, it is clear that there are more than two types of 5-HT binding sites. Evidence suggests the existence of several subpopulations of receptors.

One such subpopulation is identified by labeling with [$^3$H]-8-hydroxy-N,N-dipropyl-2-aminotetralin (HDAT), referred to as 5-HT$_{1A}$ receptors. See Gozlan et al., "Identification of presynaptic serotonin autoreceptors using a new ligand: $^3$H-PAT", Nature (1983) 305:140-143. The receptor is distinct from 5-HT$_{1B}$ and 5-HT$_2$ receptors that have been defined in brain membranes and does not appear to be related to M or D serotonergic receptors that have been identified in the periphery. The anxiolytic effects of buspirone and TVX Q 7821 appear to be mediated by central 5-HT$_{1A}$ receptors. See, Peroutka, "Selective Interaction of Novel Anxiolytics with 5-Hydroxytryptamine$_{1A}$ Receptors", *Biol. Phychiatry* (1985) 20:971-979. Interaction of antimigraine drugs with 5-HT$_{1A}$ receptors has also been demonstrated. See, Hiner et al., "Antimigraine Drug Interactions with 5-Hydroxytryptamine$_{1A}$ Receptors", *Annals of Neurology* (1986) 19:511-513. Chemical structures of compounds that interact with 5-HT$_{1A}$ receptors vary widely. Buspirone, TVX Q 7821, methylsergide, cyproheptadine, pizotifen, and (-)-propranolol are all potent inhibitors of [$^3$H]-8-OH-DPAT binding to 5-HT$_1$A receptors.

A particularly desirable characteristic for a 5-HT$_{1A}$-binding molecule, in addition to high binding affinity, is selectivity specifically for 5-HT$_{1A}$ receptors in preference to other 5-HT receptors. Additional classes of compounds other than those already known that can be readily prepared and which have the desired selectivity will greatly extend the therapeutic uses of 5-HT$_{1A}$-binding compounds.

SUMMARY OF THE INVENTION

The present invention provides a class of 5-HT-receptor-binding compounds that are capable of selectively binding with the 1A receptor in preference to other 5-HT receptors. These compounds have the formula

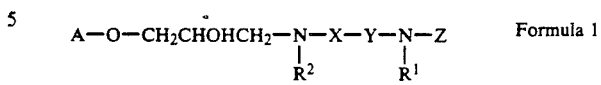

$$A-O-CH_2CHOHCH_2-N-X-Y-N-Z \quad \text{Formula 1}$$
$$\phantom{A-O-CH_2CHOHCH_2-N-}R^2 \phantom{-X-Y-}R^1$$

wherein A is an aromatic group selected to provide, with the glycidyl residue that forms the next portion of the molecule, a 5-HT-like portion of the molecule that represents the primary binding site of the molecule with a 5-HT receptor. The remainder of the molecule comprises a diamine at the end of the glycidyl side chain that modifies binding to select specifically for the 5-HT$_{1A}$ receptors. The diamine can be unsubstituted or can be terminally substituted with an alkylating or other binding group to provide for covalent or otherwise prolonged binding. The substituents R$^1$ and R$^2$ on the nitrogens are generally hydrogen but can represent small organic residues, typically methyl. A linking group X-Y between the two nitrogens of the diamine comprises two portions, a proximal portion X comprising a quarternary carbon attached to the proximal nitrogen of the diamine, and a distal portion Y that can vary significantly in length and/or bulk while still providing the desired selectivity. Compounds of the invention can be used to interact with 5-HT$_{1A}$ receptors in a variety of pharmacological situations.

DESCRIPTION OF SPECIFIC EMBODIMENTS

Investigations in the laboratories of the present inventors have uncovered a new class of compounds active as 5-hydroxytryptamine$_{1A}$ receptors. These compounds resemble propranolol in that they comprise an aromatic phenol (naphthol in propranolol) attached as an ether to an aminohydroxypropyl group (1-amino-2,3-dihydroxypropane in propranolol). They differ from propranolol, however, in having the terminal amino group of the aminohydroxypropyl group replaced by a diamine. The proximal amino group of the diamine replaces the terminal amino group of propranolol or of a related compound with a different aromatic group (particularly propranolol-like compounds known to have high affinity for 5-HT receptors). The distal amino group of the diamine is attached to the proximal amino group by means of a two-part linking group X-Y in which the proximal X portion is a sterically hindered carbon, particularly a quarternary carbon. The distal Y portion of the linking group can vary widely in length, polarity, and/or bulk as described below. The two amino groups can be substituted by small organic groups, particularly methyl, although hydrogens are preferred. The distal amino group can also be bonded to a strong-binding group, such as an alkylating group that will react with amino acid side chains or otherwise interact with the receptor to provide strong binding.

The diamine portion of the molecule appears to direct binding specifically to 5-HT$_{1A}$ receptors in preference to other 5-HT receptor types. This selectivity is believed to be based on differences in steric structure at moderate distances from the primary binding site that is believed to be in the region of the aromatic ring (and possibly the hydroxypropyl side chain), which is responsible for binding to all types of 5-HT receptors.

Propranolol-like molecules typically have an aromatic group selected from (1) fused bicyclic aromatic rings comprising 5- to 7-membered rings (preferably 5- or 6-membered rings) and 0 to 4 (preferably 0 or 1) heteroatoms and (2) monocyclic aromatic rings containing one 5- or 6-membered ring and 0 or 1 heteroatoms and having a hydrocarbon-containing side chain with at least one site of unsaturation and 0 to 2 heteroatoms. It is not required that all atoms of the rings be involved in the aromaticity of the aromatic ring system. Typical fused bicyclic aromatic rings include naphthalene, indene, benzofuran, benzothiofuran, indole, indolenine, 2-isobenzazole, benzoxazole, Tetralin, Decalin, 1,2-benzopyran, coumaran, quinoline, isoquinoline, cinnoline, pyrido[3,4-b]pyridine, and purine. Typical monocyclic aromatic rings include benzene, furan, thiophene, pyrrole, and thiazole substituted with $C_2$–$C_4$ alkyl, alkenyl, or alkynyl groups optionally containing oxygen (in the chain to form an ether or as a functional group, typically hydroxy, oxo, or carboxy), or a corresponding nitrogen- or sulfur-containing moiety.

Attachment of the hydroxypropyl side chain to the aromatic group typically occurs at a position ortho to a fused ring or ortho or meta to a side chain for monocyclic aromatics. For example, the following positions are preferred for the indicated residues: 1-naphthyl: 4-indolyl: 2-allylphenyl.

Additionally, the aromatic group can be substituted. Typical aromatic substituents can be present on the rings and typical non-aromatic substituents can be present at other locations. Typical aromatic substituents include alkyl, alkenyl, alkynyl, cyano, halo, acyl (especially alkanoyl), carboxy, hydroxy, amino, hydrocarbyloxy (especialy alkyloxy), mono- and di-alkylamino, amido, nitro, and other well-known aromatic substituents, preferably containing two or fewer carbons, more preferably 1 or 0 carbons. More than one functional group may be present in a substituent (e.g., —NHCOCH$_2$Br). Typical non-aromatic substituents include those specifically named as aromatic substituents (except nitro). Unsubstituted aromatic rings (except for the required unsaturated side chain of monocyclic aromatic rings) are preferred.

Particularly preferred are aromatic rings of the formula below

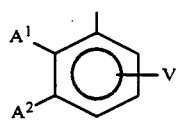

Formula 2 in which $A^1$ and $A^2$ together represent —CH=CH—CH=CH— or —CH=CH—NH—. V is an optional aromatic substituent (see above), preferably cyano and more preferably H (i.e., the aromatic ring is unsubstituted). V can be present either in the indicated phenyl ring or in the second ring formed by $A^1$ and $A^2$ (V in the second ring is preferred, most preferably at the 2-position in an indole). $A^1$, in this grouping, also can represent —CH$_2$—CH=CH$_2$ while $A^2$ represents H.

The stereochemistry of the hydroxypropyl-derived portion of the molecule is not specified in the formulas above. The same stereochemistry present in (—)-propranolol is preferred, although mixtures of isomers can produce the desired effect by reacting through their member having the correct stereochemistry.

Synthesis of compounds of the invention is discussed in more detail below. However, a brief overview of a typical synthesis is useful at this point for showing variations in structure and indicating why the side chain is said to be extended by a diamino compound.

A typical synthetic route to compounds of the invention is set forth in the formula below:

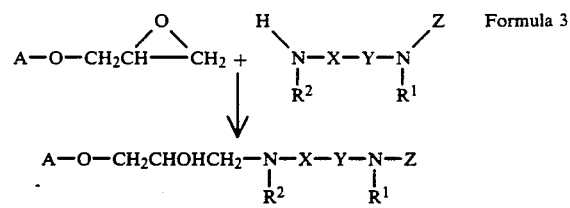

Formula 3

The glycidyl ether is a commonly used reactive functional group and can itself be prepared in a number of ways, most typically by reaction of an hydroxy-bearing aromatic compound with epichlorohydrin. The resulting glycidyl group is then reacted with the diamine under standard conditions.

If only one hydrogen is present on one of the two amino groups of the diamine, as shown in Formula 3, reaction can occur at only one end of the molecule. Such a synthetic route provides an unambigous product. However, it is also possible to carry out the reaction with hydrogens on both amino groups, followed by separating the two products from each other, although a free distal amine may prove difficult to separate from its isomers, such compounds can typically be acylated (e.g., acetylated) to provide more readily crystallizable materials and thus can be easily separated, if necessary hydrolyzing back to the free amine.

The X-portion of the diamine comprises a sterically hindered carbon, either a tertiary carbon or more preferably a quarternary carbon. This portion of the molecule will therefore typically have the formula

Formula 4 in which at least one of $X^1$ and $X^2$ represents an alkyl group with the other being hydrogen and more preferably representing a second alkyl group. Relatively small groups, such as propyl, ethyl, and methyl (in increasing order of preference) are preferred. A —C(CH$_3$)$_2$group is most preferred as X.

The Y-portion of the diamine can vary significantly in structure but is typically hydrocarbon, although typical organic substituents and functional groups, such as those previously discussed, can also be present (preferably 3, more preferably 2, or fewer). Y can be as simple as a methylene group or can contain up to 10 carbons, preferably in the form of a linear chain of methylene groups or a 5- to 7-carbon cycloalkyl group, either of which can optionally be substituted with 1 to 3 methyl, ethyl, propyl, or isopropyl groups. Preferred cycloalkyl groups have a substitution pattern that places the amines as widely removed from each other as possible (1,4-substitution in a 6-membered ring: 1,3-substitution in a 5-membered ring: etc.). Preferred is a 1,4-cyclohexyl group, optionally with an additional methyl group at the 4 position (geminal to the distal nitrogen). The total number of atoms in the shortest chain linking the two amino groups of the diamine is typically 2-8, preferably 2-6, more preferably 2-5. Unsaturation be present in the Y group, preferably not so as to provide an enamine.

The distal nitrogen can be present as a free amino group or can be substituted with a variety of substituents ranging widely in bulk and polarity, without adversely affecting selectivity for the 5-HT$_{1A}$ receptor. For example, acyl groups varying from bromoacetyl to bicyclo[2.2.2]octa-2,5-diene-2-carbonyl to methoxycarbonylacrylyl (the monomethyl ester of a fumaric acid residue) have been demonstrated to exhibit both high binding and specificity for the 1A receptor. Accordingly, it appears that the distal amino can accommodate a variety of substituents, containing up to 12 carbon or organic hetero (N, O, S) skeletal atoms, optionally substituted with halogen. Skeletal atoms are covalently linked atoms other than hydrogen. Up to 4 of the skeletal atoms can be heteroatoms, which can be present in various functional groups, as previously discussed.

Preferred are acyl (carboxylic acid derivative) compounds of the following formulas:

alkyl or alkenyl group bridging the carbon or carbons to which the two $Z^2$'s are attached to form a 5- or 6-membered cyclic ring. When —$CO^2Z_3$ is present, preferably only one such group is present, and it is present in a $\beta$ position.

Examples of specific compounds of the invention include the following:

A—O—CH$_2$CHOHCH$_2$—N—X—Y—N—Z
                      |        |
                      R$^2$     R$^1$

| | A | X | Y | Z | R$^1$ | R$^2$ |
|---|---|---|---|---|---|---|
| 1. | 4-indolyl | —C(CH$_3$)$_2$— | | 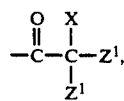 | H | H |
| 2. | 1-naphthyl | —C(CH$_2$CH$_3$)$_2$ | —CH$_2$CH$_2$— | —COCH=CHCO$_2$CH$_3$ | —CH$_3$ | H |
| 3. | 2-allylphenyl | —C(CH$_3$)(CH$_2$CH$_3$)— | —CH$_2$— | 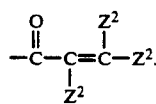 | H | —CH$_2$CH$_3$ |
| 4. | 4-(2-cyano)indolyl | —C(CH$_3$)$_2$— | —(CH$_2$)$_4$— | —COCCl$_3$ | H | H |
| 5. | 2-allylphenyl | —C(CH$_3$)$_2$— | —CH$_2$— | —COCH$_2$Br | H | H |
| 6. | 2-allylphenyl | —C(CH$_3$)$_2$— | —CONHCH$_2$CH$_2$— | COC(CH$_3$)$_2$NH$_2$ | H | H |
| 7. | 2-allylphenyl | —C(CH$_3$)$_2$— | —C(CH$_3$)$_2$— | H | H | H |
| 8. | 4-indolyl | —C(CH$_3$)$_2$— | —CH$_2$—⟨C$_6$H$_4$⟩— | —COCH$_2$Br | H | H |
| 9. | 3-vinylaminophenyl | —C(CH$_3$)$_2$— | —⟨C$_6$H$_4$⟩— | —CO-cyclohexenyl-diiodo | H | H |
| 10. | 5-cinnolinyl | —C[C(CH$_3$)$_2$]$_2$— | —(CH$_2$)$_3$— | H | —CH$_3$ | —CH$_3$ |

Formula 5

$$-\overset{O}{\underset{}{C}}-\overset{X}{\underset{Z^1}{C}}-Z^1,$$

Formula 6

$$-\overset{O}{\underset{}{C}}-\overset{Z^2}{\underset{Z^2}{C}}=C-Z^2.$$

In these compounds X represents a halogen, typically bromine or chlorine, and $Z^1$ represents hydrogen, an alkyl group, or a halogen. $Z^2$ represents hydrogen, an alkyl group, or —CO$_2Z^3$, in which $Z^3$ represents an alkyl group, or any two $Z^2$ can represent a divalent Throughout this application, if no indication of size is given for an alkyl group or other hydrocarbyl group, preferred sizes are from 1 to 6 carbons, more preferably from 1 to 4 carbons. Hydrocarbyl groups can include carbon-carbon double bonds and carbon-carbon triple bonds, unless specifically noted as being otherwise.

Throughout this application and particularly with regard to the structure of the compounds set forth above, groupings of substituents (or other limitations) intended to define preferred embodiments of the invention can be selected independently. For example, a particularly preferred aromatic group can be combined with typical groups at other positions to provide a grouping of compounds of intermediate preference. All such combinations, including combinations formed eliminating one or more specific items from a listing of items, are contemplated as providing different groupings of compounds of the invention.

It is also contemplated that one skilled in the art will apply that skill to the practice of the invention using the techniques described herein to determine optimum operating characteristics for compounds of the invention. For example, compounds can be used in any pharmaceutical application for which compounds that interact with 5-HT$_{1A}$ receptors are now known to be effective. The typical action of the compound is to block or compete with endogenous compounds that bind to 5-HT$_{1A}$ receptors, particularly serotonin. Some variation in dosage or administration regimen is to be expected, but optimum doses and administration regimens can be determined using the general guidelines set forth herein that provide a set of initial conditions. For example, Hiner et al., *Annals of Neurology* (1986) 19:511-513, describes interactions of four antimigraine drugs with 5-HT$_{1A}$ receptors in rat brain membranes. This model can be used in combination with other known techniques to optimize administration in a pharmaceutical regimen. For example, cellular concentrations of approximately 10 nM can be used as an initial concentration value followed by adjustment as necessary to provide the desired level of activity. To achieve this concentration of the drug at the cellular level, the drug can be administered at an initial dosage of 10-15 nanomoles per kilogram of body weight, followed by adjusting the dosage rate in response to analytically determined levels, the analysis typically being made on a blood sample. Final adjustment of the dose to be administered can be made by monitoring the desired effect.

Compounds of the present invention can be administered to a variety of hosts for a number of different pharmaceutical purposes. For example, compounds of the invention can be used as antimigraine drugs and as anxiolytics. Significant effects on thermoregulation (i.e., cooling), blood pressure (reduction), and sexual behavior have also been noted for compounds that bind with 5-HT$_{1A}$ receptors. Antidepressant activity has also been noted. Possible hosts include humans and domesticated animals, such as cattle, horses, dogs, chickens, cats, goats, turkeys, and pigs.

The drugs either by themselves or in combination may be administered subcutaneously, intradermally, orally, parenterally, intraperitoneally, intravascularly, or by any other suitable means. The particular manner of administration will be selected in order to ensure that the drug or drugs are able to be directed to the site of desired action in an effective dosage.

The subject drugs can be formulated in conventional manners employing a physiologically or pharmacologically acceptable carrier. Such carriers include aqueous solutions, where the drug may be suspended (optionally employing a surfactant or emulsifier) or dissolved. Aqueous and non-aqueous solvents and suspending agents include phosphate-buffered saline, dimethylsulfoxide (DMSO), ethylene glycol, and ethyl alcohol. The drug can be formulated as a tablet, capsule, or the like, being encapsulated in accordance with conventional techniques. Compounds of the present invention can be formulated and utilized in the same manner as other compounds intended for the same purposes, as set forth above. For example, formulations, dosages, techniques suitable for oral administration, and the like for anxiolytics, including benzodiazapines and related compounds, can be found in the Pharmacological Basis of Therapeutics, 5th ed., Goodman and Gillman, eds. McMillan Publishing Company, N.Y., 1975. Formulation and administration is therefore within the skill of those skilled in the art to which this invention pertains. However, the following comments are provided for initial guidance.

The concentration of the drug in a particular formulation will vary depending upon the formulation, the presence or absence of other drugs, the manner of administration, the carrier, and the like. Typical unit dosages will fall in the range of from about 0.1 to about 50 mg of active ingredient. Orally administratable tablets and capsules containing from 5-95% active ingredient are suitable. Parenteral compositions containing 1-100 mg/ml can readily be prepared. Sterile dry powders for use as intravenous injection solutions upon mixing with physiological saline are likewise suitable.

The dosage of the subject compounds will generally be at least about 0.1 and not more than about 200 mg/kg of body weight per day in single or multiple doses, usually from about 1-100 mg/kg of body weight. The treatment course can be given for a day, a few days, weeks, months, or years, depending upon the effectiveness of the course of treatment or the refractory nature of the disease.

The subject compositions can be administered in conjunction with, either in the same formulation or in a separate formulation, other drugs which act in cooperation with the drugs of the subject invention or may be employed to provide for various supportive propylaxis or therapeutic capabilities.

The invention now being generally described, the same will be better understood by reference to the following examples which are provided for purposes of illustration and are not to be considered limiting of the invention unless so specified.

EXPERIMENTAL

Example 1

Chemical Synthesis

A number of compounds were synthesized to demonstrate the synthetic techniques for preparing compounds of the invention using 1,8-diamino-p-menthane as the diamino compound. Pindolol and cyanopindolol with an aminohydroxypropyl side chain were used as the pharmacophore. Structures of compounds including reference numbers referred to in later specific synthetic techniques are set forth below.

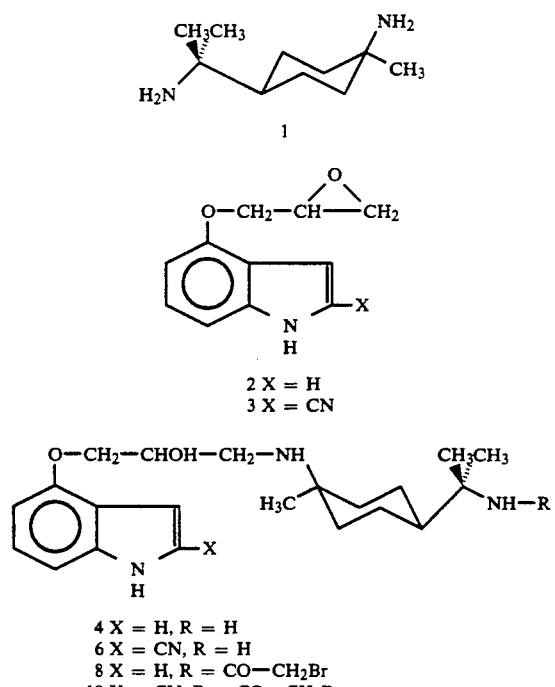

-continued

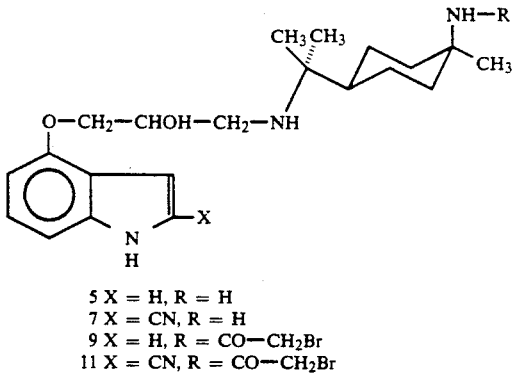

5 X = H, R = H
7 X = CN, R = H
9 X = H, R = CO—CH$_2$Br
11 X = CN, R = CO—CH$_2$Br

Chemistry

Commercial reagent grade chemicals were used in the syntheses. Thin-layer chromatography was performed on EM Reagents precoated silica gel sheets (60F-254, 0.2 mm, EM Reagents). Silica gel grade H60, 230–400 mesh (Merck Co.), was used for column chromatography. Nuclear magnetic resonance spectra were measured at 60 MHz on a JEOL PMX-60 spectrometer in deuteriochloroform or deuterioacetone with tetramethylsilane as the standard. Elemental analytical results were within 0.4% of theoretical values except where indicated. Compounds 4–11 were amorphous and occluded solvents tenaciously. Compounds 8–11 had a tendency to decompose, which further complicated their identification by mass spectrometry. Molecular ion peaks were present only in some of the MS (70 eV) spectra of the same samples. Ions, which were obviously formed through the decomposition of dimerized species, were detected in MS (PD, Cf-252) and in MS (FAB, Xe8KeV) spectra, and these were again absent in MS (CI, NH$_3$) spectra of the same samples.

Glycidyl 4-Indolyl Ether (2) and Glycidyl 2-Cyano-4-indolyl Ether (3)

Commercial 4-hydroxyindole was converted to compound 2 by reflux (2 hrs) in epichlorohydrin (17 molar excess) with a catalytic amount of 1-methylpiperazine. Compound 2 was purified by chromatography on silica gel with chloroform-methanol (98:2) as eluent, yield 65%, mp 63° C.

Compound 3 was prepared from commercial 2-methyl-3-nitrophenol by conversion to 4-(benzyloxy)indole-2-carboxylic acid in three steps using the technique of Stoll et al., Helv. Chim. Acta (1955) 38: 1452. Treatment of this acid with SOCl$_2$ in dichloromethane containing a catalytic amount of dimethylformamide for 3 hrs at room temperature converted it to the acid chloride, which, after dissolution in dichloromethane, was treated with anhydrous NH$_3$ in diethyl ether at −20° C. and thus converted to an amide, mp 185°-187° C. (ethanol-water), in 79% overall yield. The amide was converted to nitrile by treatment with trifluoroacetic acid anhydride in pyridine for 2 hrs at 0° C. with a yield of 83%: mp 125°-128° C. (benzene-hexane). Debenzylation was difficult to achieve: in the final procedure 2-cyano-4-(benzyloxy)indole (248 mg, 1 mM), ammonium formate (315 mg, 5 mM), and Pd (5%) on carbon (200 mg) in methanol (20 ml) were stirred for 1 hr at room temperature and then refluxed until the starting material was undetectable (TLC, chloroform-methanol, 9:1). Column chromatography on silica gel with chloroform-methanol (95:5).as the eluent was used to purify the product: yield (129 mg) 82%: mp 188°-190° C. (benzene methanol). 2-Cyano-4-hydroxyindole was refluxed in epichlorohydrin (10 molar excess) with a catalytic amount of morpholine until the starting material was consumed (about 2.5 hrs), yielding, after silica gel chromatography with chloroform as an eluent, Compound 3 (175 mg 75%): mp 152°-153° C. The same reaction, when attempted in the presence of equivalent amounts of alkali, yielded complex mixtures.

N-[3-(4-Indolyloxy)-2-hydroxypropyl]-(Z)-1,8-diamino-p-menthane (4, 5)

Z diastereomer 1 was isolated from commercial 1,8-diamino-p-menthane (5 g) by flash chromatography: the column (300 g of silica gel) was eluted with ethanol-concentrated NH$_4$OH (8:2). Upon thin-layer chromatography the Z diastereomer had an R$_f$ of 0.60, while the E diastereomer had an R$_f$ of 0.39 in the same solvent system as above. Compounds ere detected with iodine vapor. Alternatively, Z diastereomer 1 was isolated by dissolution of commercial 1,8-diamino-p-menthane (23 ml) in a mixture of diethyl ether (30 ml) and n-hexane (50 ml) and cooling the solution to about −40° C. Z diastereomer 1 crystallized and was separated by filtration at low temperatures, yielding about 3 g of product.

A mixture of (Z)-1,8-diamino-p-menthane (1: 1.022 g, 6 mM) and 4-[(2,3-epoxypropyl)oxy]indole (2: 189 mg, 1 mM) was stirred in an oil bath at 70° C. for 5 hrs. Excess diamine was removed by distillation [80° C. (2 mm Hg)] and the residue was purified by column chromatography with ethanol-NH$_4$OH (95:5) as the eluent. The main product (mixture of 4 and 5: 234 mg 65% yield) had an R$_f$ of 0.39 (the same eluent as used for the column) and formed a white foam: mp 55°-62° C. Analysis indicated that the product is the carbonate of 4 and 5. Anal. (C$_{43}$H$_{68}$N$_6$O$_7$) C, N, N. Subsequently, the sample (100 mg) was evaporated with 1% HCl in 70% ethanol (5 ml), and the residue was dried in vacuo, leaving dihydrochloride dihydrate. Anal. (C$_{21}$H$_{39}$Cl$_2$N$_3$O$_4$) C, H, N. Result of integration of nuclear magnetic resonance signals confirmed that this product has a 1:1 ratio of indole and p-menthane moieties. The side product had an R$_f$ of 0.70 and the above ratio of indole and p-menthane moieties was 2:1. For further identification, the desired compounds 4, 5 were derivatized. The amine (0.085 g, 0.24 mM) and 2,4-dinitrofluorobenzene (0.05 g, 0.27 mM) were heated under reflux in acetonitrile (10 ml) in the presence of sodium bicarbonate (0.2 g). After 5 hrs the solution was cooled and filtered, the precipitated salts were washed with methylene chloride, and the combined filtrates were evaporated. The remaining yellow oil was separated on a column of silica gel (10 g) with methylene chloride-methanol (96:4). Two isomers were obtained as amorphous solids. One isomer had an R$_f$ of 0.49 in chloroform-methanol (9:1) and altogether 0.043 g (35%) was obtained. MS (CI, NH$_3$) (M +H)$^+$ at m/e 526. The other isomer had and R$_f$ of 0.33 in the same system and altogether 0.037 g (30%) was obtained. MS (CI, NH$_3$) (M+H)$^+$ at m/e 526.

N-[3-[(2-Cyano-4-indolyl)oxy]-2-hydroxy propyl]-(Z)-1, 8-diamino-p-menthane (6, 7)

The above procedure was repeated with 2-cyano4-[2,3-epoxypropyl)oxy]indole (3: 0.745 g, 3.48 (Z)-1,8-diamino-p-menthane (3 ml, 2.742 g, 16.71 mM), yielding a mixture of 6 and 7 (1.1 g 77%) in the form of an off-white foam, $R_f$ 0.94 in the same system as above. The corresponding hydrochloride was prepared by evaporation of a solution of base 6/7 in methanol with hydrochloric acid (5%) and drying in vacuo, 120° C., 0.5 hrs. Anal. ($C_{22}H_{34}Cl_2N_4O_2$) C, H: N: calcd, 12.25: found, 11.83. NMR spectra were used to confirm 1:1 stoichiometry in the products. The side product had an $R_f$ of 0.67 and, as was obvious from NMR spectra, arose from the reaction of two epoxide molecules with one of diamine. Dinitrophenyl derivatives of the amines 6, 7 were obtained by the same procedure as above. One of them (yield 37%) had an Rf of 0.53 in the same solvent system. MS (CI, $NH_3$) (M H) at m/e 551. The other (yield 34%) had an $R_f$ of 0.42. MS (CI $NH_3$) $(M+H)^+$ at m/e 551.

$N^8$-(Bromoacetyl)-$N^1$-[3-(4-indolyloxy)-2-hydroxypropyl]-(Z)-1,8-diamino-p-menthane (8) and $N^1$ (Bromoacetyl)-$N^8$-[3-(4-indolyloxy)-2-hydroxypropyl]-(Z)-1,8-diamino-p-menthane (9)

The mixture of compounds 4 and 5 (1.56 g, 4.39 mM) was dissolved in anhydrous tetrahydrofuran (70 ml) and cooled in an ice bath. Bromoacetyl bromide (0.39 ml, 0.91 g, 4.5 mM) was then added dropwise and the mixture was stirred for an additional 25 min. Solvent was partially evaporated in vacuo to about a fifth of the original amount, ethyl acetate (120 ml) was added, and the solution was washed with aqueous sodium bicarbonate (20 ml, 8%), water (twice×20 ml), and dried over anhydrous sodium sulfate. Evaporation of the solution yielded an off-white foam (1.95 g, 93%) containing, according to thin-layer chromatography, two main components. These were separated on a silica gel column (60 g) eluted with chloroform-methanol (85:15). The compound eluting first, 8, formed a white foam (520 mg, 25%), $R_f$ 0.50 (chloroform-methanol, 75:25). To obtain an acceptable analysis the foam was dissolved in methanol and this solution, with stirring, was added to distilled water. The resulting suspension was freeze-dried. Compound 9 was also a white foam (560 mg, 27%), $R_f$ 0.36 in the same system.

$N^8$-(Bromoacetyl)-N1-[3-[(2-cyano-4-indolyl)oxy]-2-hydroxypropyl]-(Z)-1,8-diamino-p-menthane (10) and $N^1$-(Bromoacetyl)-$N^8$-[3-[-(2-cyano-4-indolyl)oxy]-2-hydroxypropyl]-(Z)-1,8-diamino-p-menthane (11)

The procedure for synthesizing compounds 8 and 9 was repeated with a mixture of 6 and 7 (1.025 g, 2.67 mM), tetrahydrofuran (45 ml), and bromoacetyl bromide (0.255 ml, 0.592 g, 2.93 mM) as starting material and yielded a mixture of 10 and 11 (1.37 g, 100%) in the form of an off-white foam, which was fractionated on a silica gel column (60 g), chloroform-methanol (92:8). Compound 10 was obtained, 0.42 g (31%), Rf 0.48. Compound 11 had an $R_f$ of 0.31 and was obtained in the form of an off-white foam (0.49 g, 36.4%) and after processing through freeze-drying as above gave 11 as hydrate (3.5 $H_2O$).

Stability of Compounds 8-11

In the solid state, compounds 8-11 showed traces of decomposition after about one month of storage at −20° C. unless rigorously dry: the decomposition seemed to be an autocatalytic process. Methanolic solutions (10 mg/ml) are suitable storage forms. When these were kept at −20° C. for three months, no decomposition was detected: at 4° C. for two months decomposition was barely detectable: at 20° C. for too months decomposition was observable but probably less than 5%.

EXAMPLE 2

A number of the compounds set forth above in Example 1 were tested for pharmacological activity along with four additional compounds. These additional compounds, identified here as Compounds 12-15, have the same general formula as set forth above in Example 1 with the following specific structures:

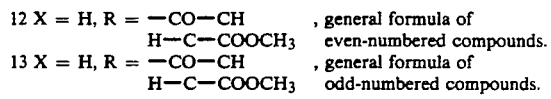
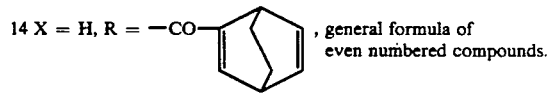

MATERIALS AND METHODS

Radioligand binding studies were performed described in Peroutka et al., Molecular Pharmacology (1979) 16:687-699. Briefly, rat brain were purchased from Pel-Freez (Roger, AR). On the day of study, the samples were thawed in Tris-HCl buffer. Tissues were homogenized in 20 volumes Tris-HCl buffer (pH 7.7 at 25° C.) using a Brinkmann Polytron and then centrifuged in an IEC B20A centrifuge at 49,000×g for 10 min. The supernatant was discarded, and the pellet was resuspended in the same volume of Tris-HCl buffer and incubated at 37° C. for 10 min prior to a second centrifugation at 49,000×g for 10 min. The final pellet was resuspended in 80 volumes of Tris-HCl buffer containing 10 $\mu$M pargyline, 4 mM calcium chloride and 0.1% ascorbic acid. The suspensions were immediately used in the binding assay. Radioligand binding studies consisted of 0.1 ml $^3$H-radioligand (0.4 nM $^3$H-8-OH-DPAT; 2 nM $^3$H-5-HT: 0.7 nM $^3$H-spiperone), 0.1 ml buffer or displacing drug and 0.8 ml tissue suspension. Following incubation at 25° C. for 30 minutes, the assays were rapidly filtered under vacuum through #32 glass filters (Schleicher and Scheull: Keene, NH) with two 5 ml washes using 50 mM Tris-HCl buffer. Radioactivity was measured by liquid scintillation spectroscopy in ml of 3a70 Counting Cocktail (Research Products International: Mt. Prospect, IL) at 54% efficiency. Specific binding was defined as the excess over blanks taken in the presence of $10^{-5}$ M 5-HT for 5-HT$_{1A}$ sites labeled by $^3$H-8-OH-DPAT, $10^{-5}$ M 5-HT$_{1A}$ for non-5-HT1A sites labeled by $^3$H-5-HT +100 nM 8-OH-DPAT, $10^{-6}$ M cinanserin for 5-HT$_2$ sites labeled by $^3$spiperone and $10^{-6}$ M propranolol for $\beta$-adrenergic receptors labeled by $^3$H-dihydroalprenolol ($^3$H-DHA). All drugs were diluted and dissolved in assay buffer.

IC$_{50}$ (50% inhibition of binding concentration) values were determined by log-logit analysis of drug competition studies. K$_i$ values were determined by the equation $K_i = IC_{50}/(1+[I]/K_D)$ where $K_D$ was 1.0 nM for $^3$H-8-OH-DPAT: 3.2 nM for $^3$H-5-HT and 0.71 nM for $^3$H-spiperone. Each experiment was performed in triplicate and repeated 3 to 6 times.

RESULTS

As shown in Table 1, three compounds are extremely potent at the 5-HT$_{1A}$ binding site (Compounds 9, 15, and 13). Moreover, these agents are approximately an order of magnitude less potent at β-adrenergic receptors labeled by $^3$H-DHA. They are approximately less potent at non-5HT$_{1A}$ binding sites and 5-HT$_2$ binding sites in rat cortex. By contrast, agents 11, 8, 14, and 12 are most selective for β-adrenergic receptors with similar, though less potent, affinity for 5-HT$_{1A}$ sites. Once again, these agents are least potent at both non-5-HT$_{1A}$ and 5-HT$_2$ binding sites.

TABLE 1

Drug Potencies at Serotinin and β-Adrenergic Receptors in Rat Cortex

| | Drug Potency (IC$_{50}$, nM) | | | |
|---|---|---|---|---|
| Compound | 5-HT$_{1A}$ ($^3$H-8-OH-DPAT) | non-5-HT$_{1A}$ ($^3$H-5-HT + 100 nM 8-OH-DPAT) | 5-HT$_2$ ($^3$H-spiperone) | β-adrenergic ($^3$-H-DHA) |
| 9 | 0.71 ± 0.02 | 430 ± 200 | 4000 ± 500 | 5.6 ± 0.5 |
| 15 | 1.1 ± 0.1 | 1300 ± 500 | — | 19.0 ± 9.0 |
| 13 | 1.2 ± 0.2 | 2900 ± 800 | 3600 ± 1000 | 10.0 ± 5.0 |
| 11 | 5.3 ± 2.0 | 410 ± 200 | 4400 ± 2000 | 1.1 ± 0.02 |
| 8 | 6.3 ± 2.0 | 140 ± 70 | 3100 ± 1000 | 1.3 ± 0.2 |
| 14 | 26.0 ± 8.0 | 46 ± 10 | — | 4.2 ± 2.0 |
| 12 | 31.0 ± 8.0 | 270 ± 50 | 1100 ± 500 | 2.8 ± 0.5 |

Radioligand studies were preformed as described in Methods. Data shown are the mean ± standard error of 3-4 experiments, each performed in triplicate on individual brian samples.

The major finding of the present study is that a class of compounds have been developed which show differential selectivity for 5-HT and β-adrenergic receptor subtypes. These compounds of the invention are particularly interesting for two main reasons. First of all, they are extremely potent at 5-HT$_{1A}$ binding sites and represent the most potent agents that have been described, to date, at this 5-HT receptor subtype. They also display marked selectivity for the 5-HT$_{1A}$ site versus other 5-HT binding type subtypes. Accordingly, they represent a class of drugs useful in replacing known 5-HT$_{1A}$ binding compounds, such as those previously mentioned.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of relieving anxiety, comprising:
   administering to a host an anxiolytically effective amount of a compound having the formula

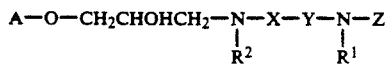

wherein A is an indolyl group optionally substituted with a cyano group;
N-X-Yn-N is a 1,8-diamino-p-menthane group;
Z is hydrogen or an acyl group of the formula

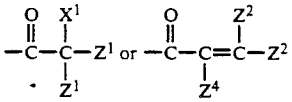

wherein:
X$^1$ is a halogen atom, each Z$^1$ is a hydrogen, a C$_1$–C$_6$ alkyl group or a halogen; each Z$^2$ and Z$^4$ are independently hydrogen, a C1–C6 alkyl group, or —CO$_2$Z$^3$ in which Z$^3$ is a C1–C6 alkyl group; or one of Z$^2$ together with Z$^4$ and the two carbons to which they are attached form a cyclohexyl or a bicyclo [2.2.2]octa-2,5-dienyl group, and
R$^1$ and R$^2$ independently represent hydrogen or C1–C6 alkyl group, in a pharmaceutically acceptable carrier.

2. The method of claim 1, wherein A represents a 4-indolyl group or a 4-(2cyanopindolol) group.

3. The method of claim 2, wherein R$^1$and R$^2$ each represent H.

4. The method of claim 3, wherein A represents a 4-indolyl group, and Z represents an acyl group of the formula —CO—CH$_2$Br.

5. The method of claim 3, w herein A represents a 4-(2-cyanopindolol) group, and Z represents an acyl group of the formula —CO—CH$_2$Br.

6. The method of claim 3, wherein A represents a 4-indolyl group, and Z represents an acyl group of the formula —CO—CH=CH—CO—O—CH$_3$.

7. The method of claim 3, wherein A represents a 4-indolyl group, and Z represents an acyl group in which one of Z$^2$ together with Z$^4$ and the two carbons to which they are attached form a bicycloc[2.2.2]octa-2,5-dienyl group and one of Z$^2$ is hydrogen.

8. The method of claim 1, wherein said host is a human.

9. The method of claim 1, wherein said amount provides a cellular concentration of approximately 10 nM.

10. A method of inhibiting binding of endogenous compounds to 5-HT$_1$A receptors, comprising:
    administering to a host in need of said binding inhibition an inhibiting amount of a compound having the formula

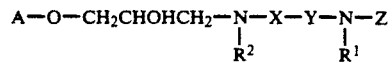

wherein
A is an indolyl group optionally substituted with a cyano group;

N-X-Y-N is a 1,8-diamino-p-menthane group;
Z is hydrogen or an acyl group of the formula

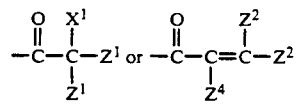

wherein:
- $X^1$ is a halogen atom, each $Z^1$ is hydrogen, a C1–C6 alkyl group or a halogen; each $Z^2$ and $Z^4$ are independently hydrogen, a C1–C6 alkyl group, or —$CO_2Z^3$ in which $Z^3$ is a C1–C6 alkyl group; or one of $Z^2$ together with $Z^4$ and the two carbons to which they are attached form a cyclohexyl or a bicyclo[2.2.2]octa-2,5-dienyl group, and
- $R^1$ and $R^2$ independently represent hydrogen or a C1–C6 alkyl group, in a pharmaceutically acceptable carrier.

11. The method of claim 10, wherein A represents a 4-indolyl group or a 4-(2-cyanopindolol) group.

12. The method of claim 10, wherein $R^1$ and $R^2$ each represent H.

13. The method of claim 12, wherein A represents a 4-indolyl group, and Z represents an acyl group of the formula —CO—$CH_2Br$.

14. The method of claim 12, wherein A represents a 4-(2-cyanopindolol) group, and Z represents an acyl group of the formula —CO—$CH_2Br$.

15. The method of claim 12, wherein A represents a 4-indolyl group, and Z represents an acyl group of the formula —CO—CH=CH—CO—O—$CH_3$.

16. The method of claim 12, wherein A represents a 4-indolyl group, and Z represents an acyl group in which one of $Z^2$ together with $Z^4$ and the two carbons to which they are attached form a bicyclo[2.2.2]octa-2,5-dienyl group and in which one of $Z^2$ is hydrogen.

17. The method of claim 4, wherein said endogenous compound is serotonin.

* * * * *